(12) United States Patent
Zhu et al.

(10) Patent No.: US 10,365,213 B2
(45) Date of Patent: Jul. 30, 2019

(54) RELIABLE FLUORESCENCE CORRECTION METHOD FOR TWO-COLOR MEASUREMENT FLUORESCENCE SYSTEM

(75) Inventors: Jiang Zhu, Beijing (CN); Cheng Deng, Beijing (CN); Guoliang Huang, Beijing (CN); Shukuan Xu, Beijing (CN); Jing Cheng, Beijing (CN)

(73) Assignee: CapitalBio Corporation, Beijing (CN)

(*) Notice: Subject to any disclaimer, the term of this patent is extended or adjusted under 35 U.S.C. 154(b) by 595 days.

(21) Appl. No.: 12/997,223

(22) PCT Filed: Jun. 11, 2008

(86) PCT No.: PCT/CN2008/001127
§ 371 (c)(1),
(2), (4) Date: Mar. 14, 2011

(87) PCT Pub. No.: WO2009/149580
PCT Pub. Date: Dec. 17, 2009

(65) Prior Publication Data
US 2011/0301062 A1     Dec. 8, 2011

(51) Int. Cl.
*G01N 33/48*      (2006.01)
*G01N 33/50*      (2006.01)
*G01N 21/27*      (2006.01)
*G01N 21/64*      (2006.01)

(52) U.S. Cl.
CPC ....... *G01N 21/278* (2013.01); *G01N 21/6452* (2013.01); *G01N 2021/6421* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 6,163,714 A * | 12/2000 | Stanley | G01N 33/54373 422/82.07 |
| 6,661,909 B2 | 12/2003 | Youvan et al. | |
| 7,209,836 B1 | 4/2007 | Schermer et al. | |
| 2003/0016882 A1* | 1/2003 | Riley | G01J 3/28 382/275 |
| 2003/0059811 A1* | 3/2003 | Djaballah et al. | 435/6 |
| 2004/0191786 A1 | 9/2004 | Yue et al. | |
| 2007/0042367 A1* | 2/2007 | Tao et al. | 435/6 |

FOREIGN PATENT DOCUMENTS

| | | |
|---|---|---|
| CN | 101042345 | 9/2007 |
| CN | 101055251 | 10/2007 |

OTHER PUBLICATIONS

Lee et al. Quantum-dot-tagged microbeads for multiplexed optical coding of biomolecules. Nature Biotechnology, Jul. 2001, vol. 19, pp. 631-635.*
Marton et al. Drug target validation and identification of secondary drug target effects using DNA microarrays. Nature Medicine, vol. 4, 1998, pp. 1293-1301.*
DeRisi et al. Exploring the metabolic and genetic control of gene expression on a genomic scale. Science, vol. 278, 1997, pp. 680-686.*
Pollack et al. Genome-wide analysis of DNA copy-number changes using cDNA microarrays. Nature Genetics, vol. 23, 1999, pp. 41-46.*
Patterson et al. Performance comparison of one-color and two-color platforms within the MicroArray Quality Control (MAQC) project. Nature Biotechnology, vol. 24, 2006, pp. 1140-1150.*
MacBeath et al. Printing proteins as microarrays for high-throughput function determination. Science, vol. 289, 2000, pp. 1760-1763.*
Okabe et al. n Genome-wide analysis of gene expression in human hepatocellular carcinomas using cDNA microarray: Identification of genes involved in viral carcinogenesis and tumor progression. Cancer Research, vol. 61, 2001, pp. 2129-2137.*
Tyagi et al. Molecular beacons: Probes that fluorescne upon hybridization. Nature Biotechnology, vol. 14, 1996, pp. 303-308.*
Vogelstein et al. Digital PCR. PNAS, vol. 96, pp. 9236-9241. (Year: 1999).*
Buschmann et al., Bioconjugate Chemistry (2003) 14:195-204.
Chen et al., Biophysical Journal (2006) 91:L39-L41.
Duggan et al., Nature Genetics Supplement (1999) 21:10-14.
Gordon et al., Biophysical Journal (1998) 74:2702-2713.
Hegde et al., Biotechniques (2000) 29:548-562.
International Search Report for PCT/CN2008/001127, dated Mar. 19, 2009, 2 pages.
International Preliminary Report on Patentability for PCT/CN2008/001127, dated Dec. 13, 2010, 6 pages.
Lee et al., Biophysical Journal (2005) 88:2939-2953.
Patterson et al., Nature Biotechnology (2006) 24:1140-1150.
Shalon et al., Genome Methods (1996) 6:639-645.
Thaler et al., Biophysical Journal (2005) 89:2736-2749.
Yang et al., Nature Review Genetics (2002) 3:579-588.
Zal et al., Biophysical Journal (2004) 86:3923-3939.
Hussain et al., "An Introduction to Fluorescence Resonance Energy Transfer (FRET)," Aug. 13, 2009, 4 pages.

* cited by examiner

*Primary Examiner* — Russell S Negin
(74) *Attorney, Agent, or Firm* — Rimon P.C.

(57) ABSTRACT

Methods and devices use in two-color measurement systems. The methods and devices include methods of making corrections, methods of calculating correction factors, fluorescence scanners, and microarray chips. The said methods and devices enable a user to correct fluorescence intensities for errors caused by the occurrence of FRET and/or crosstalk when two fluorophores are used in two-color fluorescence arrays.

10 Claims, 4 Drawing Sheets

Specification includes a Sequence Listing.

|  | Cy5 channel | Cy3 channel | FRET channel |
|---|---|---|---|
| Cy5-dsDNA-NH₂ chip | (a) | (b) | (c) |
| Cy3-dsDNA-NH₂ chip | (d) | (e) | (f) |
| Cy5-dsDNA-Cy3-NH₂ chip | (g) | (h) | (i) |

Figure 2

RELIABLE FLUORESCENCE CORRECTION METHOD FOR TWO-COLOR MEASUREMENT FLUORESCENCE SYSTEM

CROSS-REFERENCE TO RELATED APPLICATIONS

This application is the national phase of PCT application PCT/CN2008/001127 having an international filing date of Jun. 11, 2008. The content of the above-listed PCT application is incorporated herein by this reference in its entirety.

TECHNICAL FIELD

This invention relates to reliable methods and systems for measuring fluorescence emissions in a two-color fluorescent labeling system and to simple methods to correct for distortions caused by fluorescence resonance energy transfer and/or cross-talk in two-color fluorescence measurements.

BACKGROUND ART

The microarray is a popular and effective tool in molecular biology, such as gene expression analysis, genome analysis and drug discovery. Microarrays are well known in fields where detection of a specific material such as a DNA or RNA sequence of interest is important, and methods for making and using microarrays are widely known and practiced. A microarray can be read or visualized in numerous ways to detect targets in the sample. One of the most convenient and selective methods for visualizing a microarray is via fluorescence, since these targets of interest frequently have low background levels of fluorescence, and since this detection method adapts well to automation.

Microarray methods make it possible to simultaneously analyze the relative amount of different targets in the sample based on the intensity of the fluorescence signals representing the relative abundance of targets (e.g., nucleic acid and protein). Typical applications include expression profiling, using cDNA microarrays. (Duggan, et al., Nature Genetics Supplement, 21: 10-14, 1999; Yang, et al., Nature Review Genetics, 3: 579-588, 2002) The probe immobilized on the microarray is commonly a known structure and is used to query the targets for the presence and the amount of a feature that is known to bind to the immobilized probe. This is done by contacting the microarray with a sample believed or suspected to contain a fluorescence-labeled target known to have a strong binding affinity for the probe. Then, if the target is present in the sample, it binds to the special probe immobilized on the chip or slide and remains affixed to the microarray. It is possible to detect a large number of targets and to sort out the relative amount of these targets in the sample simultaneously, based on the fluorescence intensities on the microarray chip.

Two kinds of procedures, one-color approach and two-color approach, can be used when planning a microarray analysis. In a one-color procedure, a single fluorescence label is used: a labeled target that is specific for the probe of interest is hybridized or bound to each microarray. In a two-color procedure, two different fluorescence labels (e.g., Cy3 and Cy5 dyes) are used to label the targets in two samples (e.g., the treatment and the control), respectively. Where only one label is used, its intensity is expected to correlate with the amount of targets present in one sample. Where two different labels are used, the relative abundance of the targets from two samples can be simultaneously determined, provided the two fluorophores do not interact with each other at all.

In a two-color procedure for microarray analyses, a microarray is manufactured by spotting probes (e.g., cDNA fragments, oligonucleotides, proteins or tissues, etc.) onto a plate, chip or slide. Commonly, for example, a slide or plate of a size suitable for use in automated sample handling systems or suitable for use in commercial fluorescence scanners will be treated to provide a 'sticky' surface. Typical examples of such treated surfaces include, for example, a poly-lysine coated plate or slide, or an aminosilane coated plate or slide, each of which is suitable for immobilizing probes. Each of two samples (e.g., treatment and control, or positive selection and negative selection targets) is labeled with one distinct fluorophore (e.g., Cy5 for the treatment and Cy3 for the control). The mixture of two fluorophore-labeled samples is reacted with a microarray having a well-defined pattern of probes affixed to its surface and available for binding. Then this chip is washed to remove unbound fluorescent-labeled targets in two samples, and fluorescent images of the microarray are acquired with two channels of a fluorescence scanner. By analyzing the scanned images, the amount or ratio (e.g., Cy5/Cy3) of the two fluorescent labels at each spot on the microarray can be calculated and normalized, and background corrections can be made if necessary. Data interpretation is performed to obtain quantitative information about a variety of biological facts, which should insure that the results attain good levels of confidence.

In two-color systems, however, the two fluorescent labels may not be entirely independent of each other. When there is any spectral overlap between these two fluorophores, and the same targets present in the two samples (only with different fluorescence labels) can be bound with the probes in the same spot area on the microarray chip, it is possible for non-radiative processes such as FRET (fluorescence resonance energy transfer or Förster resonance energy transfer) to occur. FRET is distance sensitive, so it is not problematic unless the two different fluorophores are in close proximity; however, it is no always possible to know the distance between the two fluorophores. In addition, if either of the two fluorescent labels is affected by the irradiation used to induce fluorescence in the other (the excitation energy), or by the fluorescence emission of the other there can also be radiative errors referred to as cross-talk. This effect could be caused by direct effects of one fluorophore on the other (e.g., emission of one label affects fluorescence of the other) or instrumental (e.g., fluorescence emissions from one label are detected in the detection channel intended for the other label.) As a result of either of these, fluorescence detection in a two-color system (using two different fluorophores having different colors by virtue of their different characteristic emission wavelengths) will be potentially distorted by FRET among different fluorophore-labeled targets and/or cross-talk.

FRET is a non-radiative process in which energy is transferred from a donor fluorophore to an acceptor fluorophore when the spectral overlap of the donor emission wavelength and the acceptor excitation wavelength exists and the two different fluorophores are near each other, typically within the 1-10 nm range. The donor fluorophore (e.g., Cy3) and the acceptor fluorophore (e.g., Cy5) are a FRET fluorophore pair. The donor will be the higher-energy/shorter wavelength fluorophore; the acceptor will be the lower energy/longer wavelength fluorophore. To the extent a FRET effect occurs, the signal observed from the donor will not accurately represent the amount of donor present: FRET will reduce the amount of observable radiative emission from the donor and distort the observed fluorescence quantities or ratios. It may also affect the apparent fluorescence yield from the acceptor, since it provides an additional source of excitation in addition to the excitation energy provided by the instrument used to observe the acceptor when donor and acceptor fluorophores are excited simultaneously by two corresponding lights.

To eliminate this distortion, appropriate fluorophores should be selected to avoid interactions, and the distance between fluorophores in the sample should be beyond the range where FRET effects are strong, i.e., the fluorophores should generally be at least about 10 nm apart. Of course, in some systems it is not possible to control the distance between the fluorophores, and certain experiments may actually cause two different fluorescent labels to be held near one another.

Cross-talk is often the result of spectral bands, either emission or absorption bands, that are wide enough to permit leakage between the excitation and/or detection of the donor fluorophore and the excitation and/or detection of the acceptor fluorophore. When scanning the two-color microarray with the donor channel of the fluorescence scanner, cross-talk is exemplified by an emission from an acceptor fluorophore that arises from excitation intended for a donor fluorophore and enters the channel for donor emission detection: if the excitation energy intended for the donor fluorophore has any spectral overlap with the absorption spectrum of the acceptor fluorophore, there is potential for fluorescence from the acceptor that would not have been seen in the typical situation where its fluorescence is solely attributable to the excitation energy intended for the acceptor. It can be the reverse when scanning the two-color microarray with the acceptor channel of the fluorescence scanner: emission from a donor that arises due to, excitation intended for the acceptor and enters the channel for acceptor emission detection.

In an ideal microarray system (including a particular combination of fluorophores, and using a fluorescence scanner), both FRET and cross-talk would be avoided, so the measured fluorescence intensities would be directly proportional to the amount of each label present in each spot of the microarray.

However, the emission and excitation spectra of most members of the fluorophores used in a two-color microarray experiment have at least some overlap, and the distance between the fluorophores can hardly be controlled, especially when the fluorescent labels are used to observe two molecules that are intended to be in close association. Thus the possible effects of FRET and/or cross-talk cannot be entirely avoided for the two-color microarray experiment where dual fluorescent labels are desirable. In order for the measurements to be meaningful in a two-color microarray experiment where FRET occurs, the donor emission should be corrected for determining the quantity of donor fluorophore present. In the previous microarray experiment, fluorescence intensities of two fluorophores are acquired through scanning the microarray chip with two channels (usually Cy3 channel and Cy5 channel) of a fluorescence scanner directly and are not corrected for the distortion of FRET and/or cross-talk.

As used herein, where two fluorophores (e.g., Cy3 and Cy5) are present together in the same spot area on the chip, the higher-energy emitter (e.g., Cy3) of the two fluorophores will be referred to as the donor fluorophore. This is because the higher-energy emitter can provide enough energy to excite the lower-energy emitter, while the lower energy emitter cannot provide sufficient energy to cause the higher-energy emitter to fluoresce.

Where it occurs, a FRET interaction between donor fluorophore (e.g., Cy3) and acceptor fluorophore (e.g., Cy5) in the microarray spot will lead to a decrease in the detected emission from the donor, because the energy of the donor can transfer energy by the non-radiative FRET pathway to the acceptor, instead of emitting a detectable photon via the desired radiative relaxation pathway. Since only photons emitted via the radiative pathway are detected by the donor channel of the fluorescence scanner (the detector that looks for photons of the wavelength that is characteristic of the donor), energy lost from the donor fluorophore via the non-radiative (FRET) pathway will not be detected, and the observed signal will under-represent the amount of donor present in the spot of the microarray.

The present invention provides a reliable measurement of the fluorescence intensities of both fluorophores in a two-color microarray experiment using a three-channel fluorescence scanner. Each channel of the scanner observes a particular emission wavelength that is associated with a particular excitation wavelength, and the combination of three channels provides sufficient information to correct the measured fluorescence intensities from the microarray for the effects of FRET and/or cross-talk. The reliable fluorescence measurement method in the microarray experiment can provide accurate intensities of two fluorophores and can be used for the accurate data analysis and reliable data interpretation in a two-color microarray analysis, by providing simple methods to correct for any distortion due to FRET and/or cross-talk.

(Donor channel refers to detection where the excitation wavelength and detected emission wavelength correspond to donor. Acceptor channel refers to detection where the excitation wavelength and detected emission wavelength correspond to those of the acceptor. FRET channel refers to detection where the excitation wavelength is selected according to the donor, and detection wavelength is selected according to the acceptor emission wavelength.)

DISCLOSURE OF THE INVENTION

Overview

The invention provides techniques and devices for reliable fluorescence measurements incorporating a correction for the occurrence of FRET effects, and optionally also a correction for cross-talk effects. We first describe the reliable fluorescence measurement method in the two-color microarray which can eliminate measurement errors caused by the FRET interactions, and then consider the measurement errors due to cross-talk. There are three main steps in certain embodiments of the invention:

(a) Determine the system-specific factors for the measurement system (including a particular combination of fluorophores, and using a specific fluorescence scanner with fixed scanning parameters);

(b) Obtain the fluorescence emission with three channels of a fluorescence scanner that provides a donor channel (e.g., Cy3 channel of a fluorescence scanner) to observe the emission of the donor fluorophore, an acceptor channel (e.g., Cy5 channel of a fluorescence scanner) to observe the emission of the acceptor fluorophore, and a FRET channel (e.g., the channel of fluorescence scanner, where Cy5 emission wavelength is associated with Cy3 excitation wavelength) to observe sensitized emission from the acceptor fluorophore induced by non-radiative energy transfer from the donor fluorophore; and (c) Calculate the entire fluorescence intensities of two fluorophores using the obtained fluorescence emission and the factors of the measurement system, according to equations and relationships described herein.

Fluorescence Correction for the Distortion Due to FRET

The donor and acceptor fluorophores can be any suitable fluorescent compounds. In some embodiments, they are selected from commercially available fluorescent dyes, including cyanine dyes, Alexa dyes, and others known in the art, e.g., Cy5_26_6, Cy5T1, Cy5T6, Cy5T7, Cy5T8, Sq5T5, Sq5T7', Sq5T8, Sq5T6, Cy5.5T8, Cy5.5T7, Sq5T2, Sq5T1, Sq5T4, Sq5T3, Sq5T10, Sq5, Cy5.5T9, Cy5.5T5, Cy5.5T10, Cy5.5, Cy5.5T12 and Cy5.5T6. Structures for these are disclosed by Tu et al. (Nucleic Acids Research, 26: 2797-2802, 1998), which is incorporated herein by reference for its disclosure of these fluors. All of these are fluorescent dyes that generally emit in the 630-700 nm wavelength range. Other fluors useful in the invention include DY-630, DiD, Dy-635, DY-640, Bodipy630/650, ATTO 655, and ATTO 680 which are disclosed by Buschmann et al. (Bioconjugate Chemisty, 14: 195-204, 2003), which is also incorporated by reference for its disclosure of these fluors. In some embodiments, the donor fluorophore is Cy3 and the acceptor fluorophore is Cy5. Cy5 and Cy3 are well known cyanine dyes, and include variations of the alkyl group and phenyl ring substitutions; representative structures are shown here:

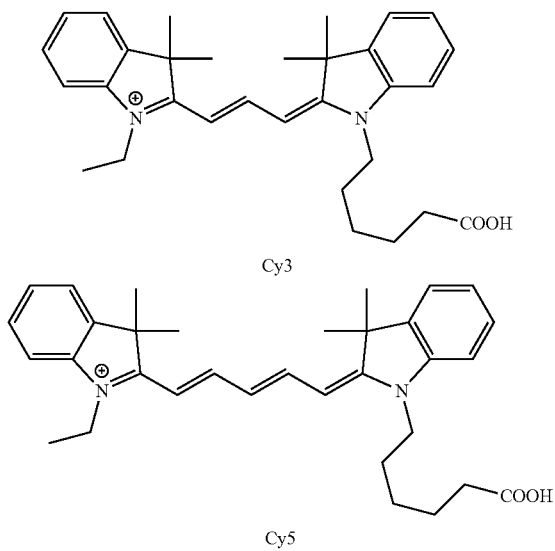

Cy3

Cy5

The values of the emission of acceptor in the absence of donor (entire acceptor emission $I_{TotalAcceptor}$, denoted I for the intensity of emission) and the emission of donor in the absence of acceptor (entire donor emission $I_{TotalDonor}$) are in direct proportion to the quantity of donor and that of acceptor, respectively, when the quantum yields of fluorophores remain constant. Under these conditions where only one fluorophore is present, no FRET occurs, and we can use the fluorescence intensity to determine the fluorescence abundance (concentration in solution or density on solid surface) of a single fluorophore. When two fluorophores are present together in the same spot of the microarray, however, FRET effects and/or cross-talk can occur. To provide accurate determinations when two fluorophores are used together in microarray experiments where they are being observed concurrently, the user must therefore correct for FRET and/or cross-talk unless the system design prevents them from making significant contributions to the observed intensities. We first describe a novel way to correct the distortion due to FRET in two-color microarray experiment, without correcting for any cross-talk.

When the overlap of emission spectrum of one fluorophore (e.g., donor) and excitation spectrum of the other (e.g., acceptor) exists in two-color microarray experiments (i.e., there is spectral overlap between the donor emission spectrum and the acceptor excitation spectrum), and two fluorophores are near each other in the spot of the microarray (i.e., the fluorophores of donor and acceptor are within about 10 nm of each other), FRET is expected to occur. The measured intensity of the spot from the acceptor channel (excitation: acceptor excitation wavelength, emission: acceptor emission wavelength), which is represented by $M_{AA}$ (denoted M for measured intensity), will be the same as entire acceptor emission $I_{TotalAcceptor}$, but the measured intensity of the spot from the donor channel (excitation: donor excitation wavelength, emission: donor emission wavelength), which is represented by $M_{DD}$, will decrease due to FRET, and will be less than the entire donor emission $I_{TotalDonor}$ because some energy of donor is non-radiatively transferred to acceptor. We also use $M_{DA}$ to represent the measured intensity of the spot from the FRET channel of the fluorescence scanner corresponds to an emission/observation where excitation is at the donor excitation wavelength, and observed emission is at the acceptor emission wavelength.

A correction for the occurrence of FRET can be made by determining a correction factor, G, which remains constant in a given two-color microarray system set-up (including a particular combination of fluorophores, and using a specific fluorescence scanner with fixed scanning parameters), and is defined by the following equation:

$$G = \frac{I_{SensitizedAcceptor}}{I_{FretDonor}^{post} - I_{FretDonor}} \quad (1)$$

where $I_{FretDonor}^{post}$ and $I_{FretDonor}$ are the direct emission of donor participating in FRET after acceptor photobleaching and before acceptor photobleaching respectively, and $I_{SensitizedAcceptor}$ is the sensitized emission of acceptor due to FRET when the spot of the microarray is excited at donor excitation wavelength.

In the typical situation, there are two kinds of donor fluorophores including a first donor fluorophore participating in FRET and a second donor fluorophore not participating in FRET, where both donor and acceptor exist in the experimental system. We call the emission from these two kinds of donor fluorophores $I_{FretDonor}$ and $I_{noFretDonor}$ respectively when the spot of the microarray is excited at donor excitation wavelength. Thus $I_{TotalDonor}$ can be determined by the following equation:

$$I_{TotalDonor} = I_{noFretDonor} + I_{FretDonor}^{post} \quad (2)$$

Combining equation 1 and equation 2 results in equation 3:

$$I_{TotalDonor} = I_{noFretDonor} + I_{FretDonor} + \frac{I_{SensitizedAcceptor}}{G} \quad (3)$$

where the sum of $I_{noFretDonor}$ and $I_{FretDonor}$ of each sample spot equals the actual direct donor fluorophore $I_{Donor}$; $I_{SensitizedAcceptor}$ of each sample spot is the actual sensitized acceptor fluorescence; and G remains constant in a given two-color microarray system (including a particular combination of fluorophores, and using a specific fluorescence scanner with fixed scanning parameters). The entire donor fluorescence $I_{TotalDonor}$ of each sample spot corrected for the influence of FRET can be determined by the equation 3. The entire acceptor fluorescence $I_{TotalAcceptor}$ of each sample spot equals the actual direct acceptor fluorophore $I_{Acceptor}$, whether donor and acceptor fluorophores participate in FRET or not.

Fluorescence Correction for the Distortion of Cross-Talk

To fully correct for errors that are likely to arise in a two-color microarray experiment, it is necessary to correct for cross-talk as well. Cross-talk arises from the spectral overlap of donor and acceptor. $I_{SensitizedAcceptor}$, $I_{Acceptor}$ and $I_{Donor}$ should be calculated by the follow equations 4, 5 and 6 with the methods described by Gordon et al. (Biophysical Journal, 74: 2702-2713, 1998):

$$I_{Sensitized Acceptor} = M_{DA} \cdot \frac{\alpha \cdot \beta - \phi \cdot \varphi}{(\alpha - \phi) \cdot (\beta - \varphi)} - M_{DD} \cdot \frac{1}{(\beta - \varphi)} - M_{AA} \cdot \frac{1}{(\alpha - \phi)} \quad (4)$$

$$I_{Donor} = M_{DD} \cdot \frac{\beta}{(\beta - \varphi)} - M_{DA} \cdot \frac{\beta \cdot \varphi}{(\beta - \varphi)} \quad (5)$$

$$I_{Acceptor} = M_{AA} \cdot \frac{\alpha}{(\alpha - \phi)} - M_{DA} \cdot \frac{\alpha \cdot \phi}{(\alpha - \phi)} \quad (6)$$

where $\alpha$ equals the ratio of signal obtained from acceptor channel to that obtained from FRET channel in the spot with only acceptor present, $\beta$ equals the ratio of signal obtained from donor channel to that obtained from FRET channel in the spot with only donor present, $\phi$ equals the ratio of signal obtained from acceptor channel to that obtained from FRET channel in the spot with only donor present, and $\varphi$ equals the ratio of signal obtained from donor channel to that obtained from FRET channel in the spot with only acceptor present, all of which are approximately constant in a given two-color microarray system (including a particular combination of fluorophores, and using a specific fluorescence scanner with fixed scanning parameters).

Because these parameters plus $\gamma$ (discussed below) provide sufficient information for making a FRET correction in a two-color fluorescence analysis when using a three-channel fluorescence scanner, in one aspect, the invention provides a novel microarray chip (or slide) that comprises the particular standard spots required for using this correction method. Thus the invention provides a microarray chip having a first spot (standard spot 1) that contains the donor fluorophore for a particular two-color system only and none of the acceptor, a second spot (standard spot 2) that contains the acceptor fluorophore for a particular two-color system only and none of the donor, and a third spot (standard spot 3) that contains both the first fluorophore (donor) and second fluorophore (acceptor) in equimolar densities. In some embodiments, the spot containing only the donor fluorophore and the spot containing only the acceptor fluorophore contain equimolar amounts of donor and acceptor, respectively. Optionally, the amount of the donor and acceptor in these two spots can be the same as the amount of donor and acceptor present in the third spot (standard spot 3) that contains a mixture of donor and acceptor together. The donor fluorophore and the acceptor fluorophore are a FRET fluorophore pair, for example the donor fluorophore is Cy3 and the acceptor fluorophore is Cy5.

Determination of the Factor G

There are several methods for the determination of the detection-correction factor G. Chen et al. (Biophysical Journal, 91: 39-41, 2006) discusses several methods, and provides a method that relies upon using two constructs that must contain each of the two fluorophores of interest for a particular system, where the two conjugates hold the fluorophores apart by different distances to produce different FRET effects. These methods all suffer from various shortcomings, such as a need for specialized equipment (e.g., one method requires measuring the quantum yields of the fluorophores, which requires a specially adapted instrument), or preparation of two or more different conjugates that contain both of the fluorophores of interest, just to determine the factor G. Herein we describe two new methods that do not require synthesis of such conjugates and can be done with the same fluorescence scanner used to make the fluorescence measurements of the microarray chip.

We define a response factor $\gamma$ as the ratio of acceptor emission in the spot with only acceptor present to donor emission in the spot with only donor present when donor and acceptor are present in the same quantity, which is a constant in a given two-color microarray system (including a particular combination of fluorophores, and using a specific fluorescence scanner with fixed scanning parameters). So the transfer factor $\gamma$ can be calculated by the equation 7 when the quantity of donor equals that of acceptor:

$$\gamma = \frac{I_{acc}}{I_{don}} \quad (7)$$

where $I_{acc}$ and $I_{don}$ are acceptor emission in the spot with only acceptor present and donor emission in the spot with only donor present, respectively.

Thus rewriting equation 3 we can calculate the factor G by equation 8:

$$G = \frac{I'_{Sensitized Acceptor}}{\frac{I'_{Acceptor}}{\gamma} - I'_{Donor}} \quad (8)$$

where $I'_{SensitizedAcceptor}$, $I'_{Acceptor}$ and $I'_{Donor}$ are the actual sensitized acceptor fluorescence, the actual direct acceptor fluorescence and the actual direct donor fluorescence of the standard spot on the microarray chip wherein the quantity of donor equals that of the acceptor, and FRET occurs between donor and acceptor.

$$\frac{I'_{Acceptor}}{\gamma}$$

is used to determine the entire donor emission in the present of FRET. If FRET does not occur, the denominator and the numerator of equation 8 will be close to zero and large calculation errors may be introduced. $I'_{SensitizedAcceptor}$, $I'_{Acceptor}$ and $I'_{Donor}$ can be calculated by the measured intensities of FRET channel, acceptor channel and donor channel using the equations 4, 5 and 6.

For the determination of the factor G and cross-talk factors in a given two-color microarray system (the system in this situation includes the fluorophores to be used and the fluorescence scanner with fixed scanning parameters), three standard spots are required, which comprise standard spot 1 containing only the donor fluorophore, standard spot 2 containing only the acceptor fluorophore in an equimolar concentration to the donor fluorophore in standard spot 1, and standard spot 3 containing the donor and acceptor fluorophores together, wherein the quantity of the donor fluorophore equals the molar quantity of the acceptor fluorophore in the third spot. Because this factor G is a useful quantity, the invention provides a microarray comprising at least one spot that contains equimolar amounts of donor fluorophore and acceptor fluorophore mixed or bound together, without other fluorescent materials in the spot. In one embodiment, this spot contains donor (e.g., Cy3) and acceptor (e.g., Cy5) admixed together in equal molar amounts, i.e., the molar amounts of the two components do not differ from each other by more than about 10%, and preferably they differ by less than about 5%.

The standard spot 3 of the microarray for purposes of the invention having equal quantities of donor and acceptor fluorophores together refers to one where the two fluorophores are present in equimolar amounts. Such samples can be made by pre-fabricating or binding a single dual-labeled molecule or complex having a 1:1 ratio of donor fluorophore and acceptor fluorophore on the microarray chip, or by applying equal amounts of the two to the same spot, or by binding a mixture of donor- and acceptor-labeled molecules in a 1:1 ratio with their complementary molecules immobilized on the microarray chip. In one embodiment, this spot is prepared by immobilizing in a spot on a microarray chip a first molecule that has one of the two fluorophores attached to it. The first molecule is selected to bind tightly to a second molecule, and the second molecule is prepared with the second fluorophore attached to it. The labeled second molecule is then brought into contact with the spot containing the labeled first molecule to form a 1:1 conjugate or hybrid molecule that contains the first and second fluorophores in equal molar amounts (a 1:1 molar ratio).

Another method comprises preparing standard spot 3 by immobilizing on the chip a conjugate comprising a complex formed by contacting the donor fluorophore linked to a first binding pair member, and the acceptor fluorophore linked to a second binding pair member complementary to the first binding pair member, wherein the conjugate comprises equimolar amounts of the donor fluorophore and acceptor fluorophore linked together by the interaction between the first binding pair member and the second binding pair member. This conjugate may be prepared in solution before it is bound to the substrate, and can be attached to the substrate by conventional methods for immobilization of such conjugates.

Another method for preparing standard spot 3 is to spot or bind dual-labeled complex on the chip. The complex is produced in solution by the method described herein for the Cy5-dsDNA-Cy3-NH$_2$ or by synthesis.

Another method is to spot or bind the mixture of a donor-labeled first binding pair member and an acceptor-labeled first binding pair member with the non-labeled second binding pair member on the chip. The donor-labeled first binding pair member and acceptor labeled first binding pair member are mixed in equimolar amounts, so they are expected to bind in equal amounts to the immobilized second binding pair member affixed onto the substrate, like the Cy5/Cy3-dsDNA-NH$_2$ described herein.

After the determination of the factor G in a given two-color microarray system (including fluorophores and the fluorescence scanner with set 1 of scanning parameters), we can determine this factor for another two-color microarray system (including the same fluorophores and the same fluorescence scanner but with set 2 of scanning parameters) by the method described below.

As β equals the ratio of signal obtained from donor channel to that obtained from FRET channel in the sample spot with only donor present, it can be written as a function of the emission properties:

$$\beta = \frac{P_D^{Donor} \cdot \eta_D \cdot \int (S_D \cdot F_D)}{P_D^{FRET} \cdot \eta_A \cdot \int (S_D \cdot F_A)} \tag{9}$$

The factor G can be described by the following equation (Zal, et al., Biophysical Journal, 86: 3923-3939, 2004):

$$G = \frac{P_D^{FRET} \cdot \phi_A \cdot \eta_A \cdot \int (S_A \cdot F_A)}{P_D^{Donor} \cdot \phi_D \cdot \eta_D \cdot \int (S_D \cdot F_D)} \tag{10}$$

Here, $P_D^{Donor}$ and $P_D^{FRET}$ are the intensity of illumination reaching the spots at donor excitation wavelength through the donor channel and FRET channel, which are relative to the excitation power in donor channel and FRET channel of the fluorescence scanner, respectively; $\eta_D$ and $\eta_A$ are the detection efficiencies through the donor channel and FRET channel, which are relative to the gains of detectors in donor channel and FRET channel of the fluorescence scanner; $\phi_D$ and $\phi_A$ are quantum yields of donor and acceptor fluorophores; $S_D$ and $S_A$ are the normalized emission spectra of donor and acceptor; $F_D$ and $F_A$ are the fractional transmissions of the band-pass filter used in the donor channel and FRET channel. Hence, the relation between the factor G and the cross-talk factor β can be described by the following equation:

$$G = \frac{\phi_A}{\phi_D} \cdot \frac{\int (S_A \cdot F_A)}{\int (S_D \cdot F_A)} \cdot \frac{1}{\beta} \tag{11}$$

where the factor G is in direct proportion to $$\frac{1}{\beta}.$$

As the parameters $\phi_D$, $\phi_A$, $S_D$, $S_A$, $F_D$ and $F_A$ remain constant for a given fluorescence scanner and fluorophore combination, and will not change with the scanning parameters of the fluorescence scanner (including excitation power of illumination and gain of the detector), the proportional coefficient H $$\left( i.e., \frac{\phi_A \cdot \int (S_A \cdot F_A)}{\phi_D \cdot \int (S_D \cdot F_A)} \right)$$

remain constant in the two-color microarray system (when maintaining the same fluorophores and the same fluorescence scanner but with optionally different scanning parameters).

We can calculate the proportional coefficient H using the known factor G and the factor $$\frac{1}{\beta}.$$

After the proportional coefficient H is determined, the factor G can be calculated simply by the factor β in the two-color microarray system (including the same fluorophores and the same fluorescence scanner) when using it with different scanning parameters. Thus only two standard spots on the microarray chip are required for the determination of the factor G and cross-talk factors when the scanning parameters of the fluorescence scanner are changed, i.e., standard spot 1 containing only the donor fluorophore and standard spot 2 containing only the acceptor fluorophore. It is not required that the acceptor fluorophore in standard spot 2 is in an equimolar concentration to the donor fluorophore in standard spot 1, which simplifies the process of changing scanning parameters as needed. However, in some embodiments the acceptor fluorophore in standard spot 2 is present in an equimolar concentration to the donor fluorophore in standard spot 1 for convenience and flexibility.

Fluorescence Correction for the Distortion of FRET and Cross-Talk

In common two-color microarray experiments, two fluorophores are used for the labeling of the samples, which are the donor fluorophore and the acceptor fluorophore of a FRET fluorophore pair (e.g., Cy3 as the donor fluorophore and Cy5 as the acceptor fluorophore). When donor- and acceptor-labeled samples are reacted with the same spot area on the chip, random close juxtapositions among different molecules can occur on a microarray chip, thus FRET can occur between the donor and acceptor even if they are coupled to different molecules. In many commercial fluorescence scanners, the emission of the spot with only acceptor present cannot be detected in the donor channel and the emission of the spot with only donor present cannot be detected with the acceptor channel, so φ and φ equal zero. In that situation, the detection-correction factor G can be determined by the following simplified equation:

$$G = \frac{M'_{DA} - M'_{DD} \cdot \frac{1}{\beta} - M'_{AA} \cdot \frac{1}{\alpha}}{\frac{M'_{AA}}{\gamma} - M'_{DD}} \quad (12)$$

where $M'_{DA}$, $M'_{AA}$ and $M'_{DD}$ are the signals from FRET channel, acceptor channel and donor channel with the standard spot 3 where the quantity of donor equals that of the acceptor, and FRET occurs between donor and acceptor.

$I_{TotalDonor}$ and $I_{TotalAcceptor}$ of the sample spot can be determined by the following simplified equation:

$$I_{TotalDonor} = M_{DD} + \frac{M_{DA} - M_{DD} \cdot \frac{1}{\beta} - M_{AA} \cdot \frac{1}{\alpha}}{G} \quad (13)$$

$$I_{TotalAcceptor} = M_{AA} \quad (14)$$

where $M_{DA}$, $M_{AA}$ and $M_{DD}$ are the signals from FRET channel, acceptor channel and donor channel with the sample spot.

In certain embodiments, the invention provides a microarray chip comprising probes that are useful for calibration of a microarray system or apparatus. The microarray chip can comprise one or more sample spots provided for the detection of targets in the test samples in addition to at least two standard spots provided for calibration of the system. In one embodiment, the chip comprises two standard spots that can be used for such calibration methods as those described herein. The first of these standard spots contains only the donor fluorophore used in the particular application and apparatus, with none of the acceptor fluorophore present; and the second of these two standard spots contains only the acceptor fluorophore, with none of the donor present. The two spots need not have the same concentrations of their respective fluorophores; but in some embodiments, the two fluorophores are present in equimolar quantity.

In another embodiment, the invention provides a microarray chip comprising three calibration standard spots. This embodiment comprises three standard spots useful for reliable fluorescence measurements, wherein the three standard spots comprise standard spot 1 containing only the donor fluorophore and no acceptor fluorophore, standard spot 2 containing only the acceptor fluorophore (with no donor) in an equimolar density to the donor fluorophore in standard spot 1, and standard spot 3 containing the donor and acceptor fluorophores together, wherein the molar quantity of the donor fluorophore equals that of the acceptor fluorophore in this spot.

These microarray chips can be used with the methods, equations and devices described herein to determine system constants (e.g., G, H, γ, α, β, φ, φ) that are needed for correcting a fluorescence measurement in a two-color microarray measurement. These microarray chips and methods for preparing them are within the scope of the invention.

For standard spot 3, having equimolar amounts of the two fluorophores of interest (a FRET fluorophore pair), the fluorophores can be separately applied to the same locus on the microarray chip, or they can be admixed and applied together. A particularly convenient method for ensuring equimolar amounts of both fluorophores are present involves immobilizing on the chip a labeled conjugate comprising either the donor fluorophore or the acceptor fluorophore linked to a first binding pair member. This conjugate is then contacted with a non-immobilized conjugate comprising the donor fluorophore (if the acceptor was in the immobilized conjugate) or the acceptor fluorophore (if the donor was in the immobilized conjugate) linked to a second binding pair member that is complementary to the first binding pair member. By doing this, the first and second binding pair members bind to each other to produce an immobilized complex having a 1:1 ratio of donor fluorophore and acceptor fluorophore.

Standard spot 1 can be produced by pre-fabricating the donor-labeled member on the microarray chip (i.e., immobilizing the fluorophore of interest on the chip by methods known in the art), or by binding donor-labeled member in a sample with a complementary non-labeled member immobilized on the chip.

Standard spot 2 can be produced by pre-fabricating the acceptor-labeled member on the microarray chip (i.e., immobilizing the fluorophore of interest on the chip by methods known in the art), or by binding acceptor-labeled member in a sample with a complementary non-labeled member immobilized on the chip.

The microarray chips described above can also contain one or more sample spots to be analyzed for the detection of targets in the test samples by a two-color microarray measurement method, in addition to the standard spots that are useful for calibration of the system. In one embodiment, once the standard spots have been applied to the microarray chip having one or more sample spots, the microarray chip is contacted with two distinguishable fluorophore-labeled samples that are adapted for the particular experiment or analysis. The fluorophore-labeled targets then bind to the probes in the sample spots if the structures of targets are present in the probes, and fluorescence measurements are then made with the three-channel detection system described herein. This microarray chip can be a stand-alone chip specifically for calibration of the system, or it can also contain a microarray of sample spots in addition to the three standard spots provided for the determination of the correction factors described herein.

Once the microarray chip has been prepared, it is scanned with the three-channel fluorescence scanner as discussed herein, and the standard spots are used to determine the correction factors to adjust measured intensities for the possible occurrence of FRET. This enables the user to determine test results for the sample spots while also gathering the calibration information needed to do the FRET corrections and/or cross-talk corrections described herein. Optionally, the microarray chips may include no sample spots; in such embodiments, the system calibration to determine correction factors needed for FRET correction is accomplished in a separate step from the collection of data for the sample spot(s). The calibration/correction factors may be determined before or after the test sample data is collected, or it may be determined concurrently with measurements made on the test sample. Once the measurements of correction factors and sample spot intensities have been made, the invention provides a method to calculate corrected intensities for the sample spots, to arrive at the reliable values that reflect the actual presence of the target structures of interest in the sample spots, without distortions caused by FRET and/or cross-talk effects. The method includes use of the equations herein to calculate corrected intensities for each fluorophore and for each spot, while applying the corrections described herein for FRET, cross-talk, or both.

In some embodiments, the fluorophore-labeled target material can be, e.g., the cDNA reverse-transcribed from RNA, a synthesized oligonucleotide, a protein, or another biopolymer such as an RNA, DNA, mRNA, tRNA, polypeptide, or oligosaccharide. Similarly, the probes pre-immobilized on the microarray chip can also be, for example, the cDNA reverse-transcribed from RNA, a synthesized oligonucleotide, a protein, or another biopolymer such as an RNA, DNA, mRNA, tRNA, polypeptide, or oligosaccharide.

The fluorescence scanner used for the invention can be a fluorescence scanner that resolves fluorescence as a function of spatial coordinates in two dimensions. In certain aspects, the invention provides a three-channel fluorescence scanner comprising:

a first fluorescence observation channel that provides excitation at a wavelength adapted for a first fluorophore, and a detector configured to detect the fluorescence wavelength of the first fluorophore;

a second fluorescence observation channel that provides excitation at a wavelength adapted for a second fluorophore, and a detector configured to detect the fluorescence wavelength of the second fluorophore; and a third fluorescence observation channel that provides excitation at a wavelength adapted for the first fluorophore, and a detector configured to detect the fluorescence wavelength of the second fluorophore. (For convenience, this description refers to a first fluorophore and a second fluorophore: it is understood that the third channel provides excitation at the donor fluorophore's absorption wavelength, and detection at the acceptor's emission wavelength.) In one embodiment, the scanner further comprises either a two-spot or a three-spot microarray slide as described herein, and is thus prepared for a correction factor determination step.

The invention provides a method for calculating corrected fluorescence intensities for donor emission in a measurement where FRET may occur, which comprises calculation of the correction factors followed by using the correction factors to calculate corrected intensities for sample spots. Accurate corrected intensity for the donor fluorophore can be calculated as follows:

$$I_{TotalDonor} = I_{Donor} + \frac{I_{SensitizedAcceptor}}{G} \quad (15)$$

$$I_{TotalAcceptor} = I_{Acceptor} \quad (16)$$

where $I_{TotalDonor}$ is the entire donor intensity of each sample spot on the microarray chip;

$I_{TotalAcceptor}$ is the entire acceptor intensity of each sample spot on the microarray chip;

$I_{SensitizedAcceptor}$ is the actual sensitized acceptor fluorescence of each sample spot due to FRET on the microarray chip;

$I_{Donor}$ is the actual direct donor fluorescence of each sample spot on the microarray chip;

$I_{Acceptor}$ is the actual direct acceptor fluorescence of each sample spot on the microarray chip;

wherein G is determined using the following relationship:

$$G = \frac{I'_{SensitizedAcceptor}}{\frac{I'_{Acceptor}}{\gamma} - I'_{Donor}} \quad (17)$$

where $I'_{SensitizedAcceptor}$ is the actual sensitized acceptor fluorescence of standard spot 3 on the microarray chip having a 1:1 ratio of donor fluorophore and acceptor fluorophore;

$I'_{Donor}$ is the actual direct donor fluorescence of standard spot 3 on the microarray chip having a 1:1 ratio of donor fluorophore and acceptor fluorophore;

$I'_{Acceptor}$ is the actual direct acceptor fluorescence of standard spot 3 on the microarray chip having a 1:1 ratio of donor fluorophore and acceptor fluorophore;

and the transfer factor γ is determined from the relationship:

$$\gamma = \frac{I_{acc}}{I_{don}} \quad (18)$$

where $I_{acc}$ is the acceptor fluorescence of standard spot 2 on the microarray chip containing only the acceptor fluorophore, and $I_{don}$ is the donor fluorescence of standard spot 1 on the microarray chip containing only the donor fluorophore, when the density of donor fluorophore in the standard spot 1 equals that of acceptor fluorophore in the standard spot 2.

In another aspect, the invention provides a method to correct a measured fluorescence emission for the occurrence of cross-talk in a two-color microarray analysis using a three-channel fluorescence scanner. The method includes at least the following steps:

(1) Providing standard spot 1 on the microarray chip containing only the donor fluorophore, and standard spot 2 on the microarray chip containing only the acceptor fluorophore;
(2) Using these standard spots to determine cross-talk factors $\phi$, $\beta$ $\varphi$ and $\alpha$, where:

$\phi$ is the ratio of the signal obtained from acceptor channel to the signal obtained from FRET channel in standard spot 1 by the fluorescence scanner;

$\beta$ is the ratio of the signal obtained from donor channel to the signal obtained from FRET channel in standard spot 1 by the fluorescence scanner;

$\varphi$ is the ratio of the signal obtained from donor channel to the signal obtained from FRET channel in standard spot 2 by the fluorescence scanner; and $\alpha$ is the ratio of the signal obtained from acceptor channel to the signal obtained from FRET channel in standard spot 2 by the fluorescence scanner. This provides the factors needed to correct for cross-talk. The user can then measure the fluorescence intensity for each sample spot on the microarray chip with donor channel to determine $M_{DD}$, with acceptor channel to determine $M_{AA}$, and with FRET channel to determine $M_{DA}$; and can correct the measured values to arrive at corrected values.

Optionally, this method further comprises using spot 3 of the three-spot standard microarray chip described above to also calculate factor G.

The user can then calculate the corrected direct fluorescence of each sample spot on the microarray chip corrected for cross-talk with these equations:

$$I_{SensitizedAcceptor} = \qquad (19)$$
$$M_{DA} \cdot \frac{\alpha \cdot \beta - \phi \cdot \varphi}{(\alpha - \phi) \cdot (\beta - \varphi)} - M_{DD} \cdot \frac{1}{(\beta - \varphi)} - M_{AA} \cdot \frac{1}{(\alpha - \phi)}$$

$$I_{Acceptor} = M_{AA} \cdot \frac{\alpha}{(\alpha - \phi)} - M_{DA} \cdot \frac{\alpha \cdot \phi}{(\alpha - \phi)} \qquad (20)$$

and $$I_{Donor} = M_{DD} \cdot \frac{\beta}{(\beta - \varphi)} - M_{DA} \cdot \frac{\beta \cdot \varphi}{(\beta - \varphi)} \qquad (21)$$

where $I_{SensitizedAcceptor}$ is the actual sensitized acceptor fluorescence of each sample spot on the microarray chip due to FRET;

$I_{Donor}$ is the actual direct donor fluorescence of each sample spot on the microarray chip;

and $I_{Acceptor}$ is the actual direct acceptor fluorescence of each sample spot on the microarray chip.

Where FRET is also possible, the microarray chip having standard spots 1, 2 and 3 can be used in place of the microarray chip having standard spots 1 and 2: standard spots 1 and 2 correspond to standard spots 1 and 2, and standard spot 3 further enables the user to determine correction factors for FRET, should it occur.

Where FRET is suspected, fluorescence of the standard spot 3 on the microarray chip with donor channel is used to determine $M'_{DD}$, with acceptor channel to determine $M'_{AA}$, and with FRET channel to determine $M'_{DA}$. These values are then corrected for cross-talk, by calculating the actual direct fluorescence of standard spot 3 on the microarray chip corrected for cross-talk using these equations:

$$I'_{SensitizedAcceptor} = \qquad (22)$$
$$M'_{DA} \cdot \frac{\alpha \cdot \beta - \phi \cdot \varphi}{(\alpha - \phi) \cdot (\beta - \varphi)} - M'_{DD} \cdot \frac{1}{(\beta - \varphi)} - M'_{AA} \cdot \frac{1}{(\alpha - \phi)}$$

$$I'_{Acceptor} = M'_{AA} \cdot \frac{\alpha}{(\alpha - \phi)} - M'_{DA} \cdot \frac{\alpha \cdot \phi}{(\alpha - \phi)} \qquad (23)$$

and $$I'_{Donor} = M'_{DD} \cdot \frac{\beta}{(\beta - \varphi)} - M'_{DA} \cdot \frac{\beta \cdot \varphi}{(\beta - \varphi)} \qquad (24)$$

where $I'_{SensitizedAcceptor}$ is the actual sensitized acceptor fluorescence of standard spot 3 due to FRET on the microarray chip;

$I'_{Donor}$ is the actual direct donor fluorescence of standard spot 3 on the microarray chip;

and $I'_{Acceptor}$ is the actual direct acceptor fluorescence of standard spot 3 on the microarray chip. These corrected values for the standard spot 3 intensities can be used to determine a FRET correction.

In many cases, there is little cross-talk between the donor and acceptor channels of the scanner, and the calculations can be simplified substantially. Accordingly, when the emission from acceptor channel in donor-only sample and the emission from the donor channel in acceptor-only sample cannot be detected in the two-color microarray experiments, the cross-talk factors $\phi$ and $\varphi$ are approximately 0. In that situation, the actual direct fluorescence of each sample spot on the microarray chip corrected for cross-talk is calculated by the following equations:

$$I_{SensitizedAcceptor} = M_{DA} - M_{DD} \cdot \frac{1}{\beta} - M_{AA} \cdot \frac{1}{\alpha} \qquad (25)$$

$$I_{Acceptor} = M_{AA} \qquad (26)$$

and $$I_{Donor} = M_{DD} \qquad (27)$$

and the actual direct fluorescence of standard spot 3 on the microarray chip corrected for cross-talk is calculated by the following equations:

$$I'_{SensitizedAcceptor} = M'_{DA} - M'_{DD} \cdot \frac{1}{\beta} - M'_{AA} \cdot \frac{1}{\alpha} \qquad (28)$$

$$I'_{Acceptor} = M'_{AA} \qquad (29)$$

and $$I'_{Donor} = M'_{DD} \qquad (30)$$

where $I_{SensitizedAcceptor}$ is the actual sensitized acceptor fluorescence of each sample spot on the microarray chip due to FRET;

$I_{Donor}$ is the actual direct donor fluorescence of each sample spot on the microarray chip;

$I_{Acceptor}$ is the actual direct acceptor fluorescence of each sample spot on the microarray chip;

$M_{DA}$ is the measured fluorescence of each sample spot from the FRET channel of the fluorescence scanner, $M_{AA}$ is the measured fluorescence of each sample spot from the acceptor channel of the fluorescence scanner;

$M_{DD}$ is the measured fluorescence of each sample spot from the donor channel of the fluorescence scanner;

$I'_{SensitizedAcceptor}$ is the actual sensitized acceptor fluorescence of the standard spot 3 on the microarray chip due to FRET;

$I'_{Donor}$ is the actual direct donor fluorescence of the standard spot 3 on the microarray chip;

$I'_{Acceptor}$ is the actual direct acceptor fluorescence of the standard spot 3 on the microarray chip;

$M'_{DA}$ is the measured fluorescence of the standard spot 3 from the FRET channel of the fluorescence scanner, $M'_{AA}$ is the measured fluorescence of the standard spot 3 from the acceptor channel of the fluorescence scanner;

and $M'_{DD}$ is the measured fluorescence of the standard spot 3 from the donor channel of the microarray. Accordingly, the user of the methods can calculate corrected intensities for each sample spot that take into account both cross-talk and FRET corrections using these equations.

For example, the invention enables a skilled person to use the actual fluorescence values $I_{SensitizedAcceptor}$, $I_{Acceptor}$ and $I_{Donor}$ determined above to calculate the entire fluorescence intensity of each sample spot on the two-color microarray corrected for FRET as well as for cross-talk. When the emission from acceptor channel in donor-only sample and the emission from the donor channel in acceptor-only sample cannot be detected in the two-color microarray experiments, again the cross-talk factors $\phi$, and $\varphi$ are approximately 0. Accordingly, the actual fluorescence values $I_{SensitizedAcceptor}$, $I_{Acceptor}$ and $I_{Donor}$ can be determined using equations 25, 26 and 27 above in order to calculate the entire fluorescence intensity of each sample spot on the two-color microarray corrected for FRET as well as for cross-talk.

In another aspect, the invention provides a method for determining detection-correction factor G, which is a system parameter that is characteristic of a fluorescence scanner for measuring fluorescence in two-color microarray experiments. One such method comprises using the actual fluorescence values $I'_{SensitizedAcceptor}$, $I'_{Acceptor}$ and $I'_{Donor}$ of the standard spot 3 determined by equations 17, 22, 23 and 24 to calculate the detection-correction factor G of the fluorescence scanner. This factor can then be used to correct measured values according to equation 15. Again, when the emission from acceptor channel in donor-only sample and the emission from the donor channel in acceptor-only sample cannot be detected in the two-color microarray experiments, the cross-talk factors $\phi$, and $\varphi$ are approximately 0. Then one can use the actual fluorescence values $I_{SensitizedAcceptor}$, $I'_{Acceptor}$ and $I'_{Donor}$ of the standard spot 3 determined from equations 28, 29 and 30 to calculate the detection-correction factor G of the fluorescence scanner, using the equation 17.

In addition, the invention provides a method to determine a new detection-correction factor G for a fluorescence measurement system from a previous G value for the same system that was operated with a different set of scanning parameters. G is a constant for the system only as long as the same fluorophores and optical and detection setups are used; changing the scanner parameters causes G to change. However, a new $G_{parameter2}$ for a given fluorescence scanner plus fluorophore combination operating with a set of scanning parameters referred to as the "parameter 2" can be determined from a corresponding G value for the same system set up with a first set of scanning parameters (parameter 1), called $G_{parameter1}$, thus avoiding the need to entirely recalculate G for the system when only scanning parameters are modified (i.e., the same fluorophore set and fluorescence scanner are used). Thus using this method, the scanning parameters can be adjusted at need without entirely redetermining the correction values discussed above.

$G_{parameter2}$ is the system parameter that is characteristic of a fluorescence scanner for measuring fluorescence in two-color microarray experiments operating with scanning parameter setup 'parameter 2', and can be determined based on the relationship:

$$G_{parameter2} = \frac{H}{\beta_{parameter2}} \quad (31)$$

where $\beta_{parameter2}$ is the ratio of signal obtained from donor channel to that obtained from FRET channel in the donor-only spot of the microarray for the fluorescence scanner set up with scanning parameter setup 'parameter 2';

H is the proportional coefficient relating the parameter 1 and parameter 2 setups of the scanner, and can be determined using the following relationship:

$$H = \beta_{parameter1} \cdot G_{parameter1} \quad (32)$$

where $\beta_{parameter1}$ can be determined by the ratio of signal obtained from donor channel to that obtained from FRET channel in the donor-only spot of the microarray for the same fluorescence scanner set up with the 'parameter 1' scanning parameters;

and $G_{parameter1}$ can be determined by the method of equation 17 or other methods for the same fluorescence scanner set up with the 'parameter 1' scanning parameters.

The parameter 1 scanning parameters can be different from the parameter 2 scanning parameters in the power of the light corresponding to donor excitation wavelength and/or the gain of the detector corresponding to donor emission wavelength and/or the gain of the detector corresponding to acceptor emission wavelength. When any of these parameters is/are modified, G will be affected. To determine G for the new setup, the user can simply calculate H for the initial setup according to equation 32, then use H and a measurement with the new parameters to calculate the new value for G from equation 31.

The methods of the invention can be used with any pair of fluorophores having well-resolved emission and excitation maxima. There should be different fluorescence properties between the two fluorophores that are to be used together, including their emission wavelength and excitation wavelength, so the two fluorophores can be separately excited and observed. In some embodiments, the emission and excitation wavelengths for the donor fluorophore are lower by at least about 30 nm than the excitation wavelength for the acceptor fluorophore. In some embodiments, the emission wavelength for the donor fluorophore is lower by at least about 50 nm than the excitation wavelength for the acceptor. Suitably, the donor/acceptor fluorophore pair can be Cy3 and Cy5 as described herein; however, other fluorophores known to be useful in microarray fluorescence analyses can be used as well.

DESCRIPTION OF THE DRAWINGS

FIGS. 2(a)-(i) show the microarray images. The respective images were obtained by scanning Cy5-dsDNA-$NH_2$ chip, Cy3-dsDNA-$NH_2$ chip and Cy5-dsDNA-Cy3-$NH_2$ chip through Cy5 channel, Cy3 channel and FRET channel. In this example, only one subarray, wherein the concentration of probe was 1.6 µM, was used for the determination of system factors. The excitation power of 532 nm and 635 nm was set to 80. The PMT gains of 570 nm and 675 nm emission channels were both set to 650.

MODES FOR CARRYING OUT THE INVENTION

Figure 1:
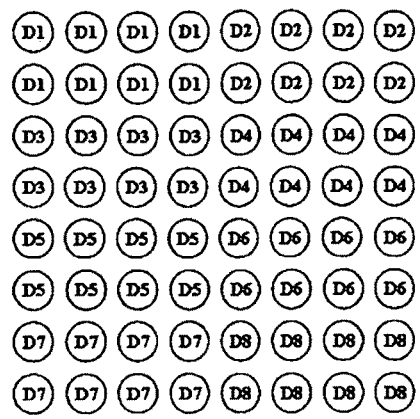
FIG. 1 shows the probe pattern of oligonucleotide (oligo-2)-$NH_2$ printed on the microarray chips with eight different subarrays. D1: 0.05 µM, D2: 0.1 µM, D3: 0.2 µM, D4: 0.4 µM, D5: 0.8 µM, D6: 1.6 µM, D7: 3.2 µM, D8: 6.4 µM.

The present invention will be described in further detail with reference to several preferred embodiments.

Terms used herein take their ordinary meanings as they would be understood in the art unless otherwise defined. Microarrays are well known in the art and are widely used, as are fluorescence scanners. Typically, microarrays are comprised of a plurality of probes distributed in a well-defined pattern or grid on a substrate that holds each probe spot in place and does not interfere with analyses to be performed on the samples. The substrate can be any suitable material, such as glass, plastic, nylon membrane or silica. The samples can be applied to the substrate by conventional methods such as spotting, printing, in situ synthesis on the substrate, or by other suitable methods known in the art.

A 'spot' as used herein refers to a discrete material on a plate or chip. A spot can be one of the sample spots of a microarray for the detection of targets in the test samples or it can be a standard or control spot for calibration of the system on a chip or plate. Typically, a microarray will include at least 96 spots, optionally it can include at least 1000 spots or more. Each spot is typically between about 1 micrometer and about 1 millimeter in its largest dimension. Technology for printing such microarrays having spots between about 10 and 500 micrometers in diameter is well known in the art.

A binding pair as used herein refers to a pair (2) of molecules or molecular fragments that have a binding affinity for each other. Each member of the pair is referred to as a binding pair member, and each member of the binding pair can be described as complementary to the other, meaning that they fit together tightly. Their affinity for each other is preferably strong enough to provide a stable complex when the two are associated together. For example, avidin or streptavidin can be a first member of a binding pair, and the second member of the binding pair could be biotin, for which avidin and streptavidin have a high affinity. Alternatively, one member could be a nucleic acid sequence of, e.g., 5-50 base pairs, and the second binding pair member could then be a complementary nucleic acid sequence having sufficient complementarity to the first member to form a stable complex. Because of their mutual affinity, the members of a binding pair can be used to link other molecules or fragments into a stable complex or conjugate. For example, the first member of a binding pair is attached to a first molecule (e.g., fluorophore 1) to form a first conjugate, and the second member of the binding pair is attached to a second molecule (e.g., fluorophore 2) to form a second conjugate. When the first and second conjugates are brought into contact, the binding affinity of the first binding pair member for the second binding pair member causes the two conjugates to be linked together into a complex, and the complex effectively links together the molecules that are conjugated to the two binding pair members; in this example, fluorophore 1 and fluorophore 2 would be held close together by the binding between the first and second binding pair members to which the two fluorophores were conjugated.

To correct the fluorescence intensities measured in a two-color microarray experiment, we first determined the system factors of the microarray scanning system used for the measurements. The examples use Cy5 and Cy3 for the labels of molecules, and a microarray scanner for the detection of fluorescence; however they are applicable to any pair of fluorescence labels that have relatively well-resolved emission and absorption maxima. Then using the reliable fluorescence measurement method with these system factors, we corrected the fluorescence intensities for the microarray chip, where Cy5 and Cy3 were bound to the same spot by hybridization. Finally, we compared the corrected ratio and uncorrected ratio of Cy5 to Cy3.

Oligonucleotides Synthesis

All oligonucleotides were synthesized and purified by high-performance liquid chromatography (HPLC) (TaKaRa Biotechnology Co. Ltd., Dalian, China). The full details are listed in Table 1.

TABLE 1

Oligonucleotides used for this study

| Symbol | | Sequence (5'→3') |
|---|---|---|
| Oligonucleotide 1 | (oligo-1)-Cy5 | TCCGTCATCGCTCAAG(-Cy5) |
| | (oligo-1)-Cy3 | TCCGTCATCGCTCAAG(-Cy3) |
| | Cy5-(oligo-1)-Cy3 | (Cy5-)TCCGTCATCGCTCAAG(-Cy3) |
| Oligonucleotide 2 | (oligo-2)-$NH_2$ | CTTGAGCGATGACGGATTTTTTTTTTTTTT(-$NH_2$) |

For this study, a Cy3 (excitation max at 550 nm, emission max at 570 nm, donor) fluorophore and a Cy5 (excitation max at 649 nm, emission max at 670 nm, acceptor) fluorophore were used.

The first set of three oligonucleotides (oligo-1) with sequence 5'-TCCGTCATCGCTCAAG-3' were synthesized respectively with Cy5 attached to the 3' terminal ((oligo-1)-Cy5), with Cy3 attached to the 3' terminal ((oligo-1)-Cy3)

and with the Cy3 attached to the 3' terminal while Cy5 attached to the 5' terminal (Cy5-(oligo-1)-Cy3).

The second set of oligonucleotides ((oligo-2)-$NH_2$) with sequence 5'-CTTGAGCGATGACG-GATTTTTTTTTTTTTTTT-3' were coupled to an aldehyde-activated glass surface as the probe by the 3' terminal amidocyanogen. The 5'-half of oligo-2 was complementary to each version of oligo-1. The 3'-half was a poly-T tail used to hold the complementary sequence away from the chip surface so that it was able to freely hybridize with the complementary oligo-1 oligonucleotides. No fluorophore was attached.

Fabrication of Microarray Chips

The oligonucleotide of (oligo-2)-$NH_2$ was diluted in DNA spotting buffer (CapitalBio Co. Ltd., Beijing, China) to fabricate the DNA microarray chip with eight subarrays, which were called (oligo-3)-$NH_2$ chip. The concentrations ranged from 0.05 μM to 6.4 μM. The pattern on the chip is shown in FIG. 1. The microarray chips were prepared using SmartArrayer™-48 microarray spotter and aldehyde-activated glass slides (CapitalBio Co. Ltd., Beijing, China).

(oligo-1)-Cy5, (oligo-1)-Cy3 and Cy5-(oligo-1)-Cy3 were respectively diluted in microarray hybridization buffer (5×Denhardt's solution, 0.2% SDS, 3×SSC in ultra-pure water) to 1.0 μM, and each of 12 μL solutions was hybridized with (oligo-2)-$NH_2$ chip to fabricate Cy5-dsDNA-$NH_2$ chip, Cy3-dsDNA-$NH_2$ chip and Cy5-dsDNA-Cy3-$NH_2$ chip. We also mixed (oligo-1)-Cy5 and (oligo-1)-Cy3 together in the same final concentration of 1.0 μM in microarray hybridization buffer and hybridized this mixture in 12 μL solution with (oligo-2)-$NH_2$ chip to fabricate Cy5/Cy3-dsDNA-$NH_2$ chip.

After hybridization at 42° C. for 2 hours, the chips were washed in washing buffer I (0.2% SDS, 2×SSC) and washing buffer II (0.2×SSC) at 42° C. both for 4 min, and then were dried by centrifugation at 1600 rpm for 1 min. Then the dried microarray chips were scanned by reconstructive LuxScan™-10K/A dual-channel laser confocal microarray scanner (CapitalBio Co. Ltd., Beijing, China), which was equipped with a third channel for the detection of FRET signal by adjusting the laser and emission filter set. The emission fluorescence was collected from three channels of the fluorescence scanner including Cy3 (donor) channel (excitation=532 nm, emission=570 nm), Cy5 (acceptor) channel (excitation=635 nm, emission=675 nm) and FRET channel (excitation=532 nm, emission=675 nm). The microarray images generated by the operational software of the scanner were analyzed by LuxScan™ 3.0 software (CapitalBio Co. Ltd., Beijing, China). Thus the images of microarray were transferred to the matrix of spot intensities.

Determination of System Factors on Microarray Chips

In FIGS. 2b and 2d, the intensities of spot are close to zero approximately, no signal can be detected from Cy5 channel in the Cy3-only sample and no signal can be detectable from Cy3 channel in the Cy5-only sample, that is, φ and ϕ equal zero. In this experiment each solution of (oligo-1)-Cy5 and (oligo-1)-Cy3 in the same concentration was hybridized with (oligo-2)-$NH_2$ chip to fabricate Cy5-dsDNA-$NH_2$ chip and Cy3-dsDNA-$NH_2$ chip. The quantity of Cy5 attached to each spot of Cy5-dsDNA-$NH_2$ chip was equal approximately to that of Cy3 attached to corresponding spot of Cy3-dsDNA-$NH_2$ chip, because the fluorophore-labeled single strand DNA molecules of (oligo-1)-Cy5 and (oligo-1)-Cy3 had the identical sequences complement with 5'-half of oligo-2 immobilized on the chip, and the same hybridization conditions were used for each reaction. The transfer factor γ can be determined from the ratio of the corresponding signal of Cy5-dsDNA-$NH_2$ chip from Cy5 channel (FIG. 2a) to that of Cy3-dsDNA-$NH_2$ chip from Cy3 channel (FIG. 2e). The cross talk factor β can be determined from the ratio of the corresponding signal from FRET channel (FIG. 2f) to that from Cy3 channel (FIG. 2e) by scanning Cy3-dsDNA-$NH_2$ chip. Similarly, the cross talk factor α can be determined from the ratio of the corresponding signal by FRET channel (FIG. 2c) to that from Cy5 channel (FIG. 2a) by scanning Cy5-dsDNA-$NH_2$ chip.

The measured intensities in equations 12, 13 and 14 can be obtained by scanning the chip through Cy3 channel, Cy5 channel and FRET channel of the fluorescence scanner, respectively.

To determine the detection-correction factor G, the density of donor should be the same as that of acceptor and FRET should occur to avoid significant measurement errors. Whether FRET occurs can be determined experimentally, by observing the FRET channel. In the examples, we hybridized Cy5-(oligo-1)-Cy3 with (oligo-2)-$NH_2$ chip to fabricate Cy5-dsDNA-Cy3-$NH_2$ chip. Because the distance between Cy5 and Cy3 was in the range of 1-10 nm according to the DNA cylindrical model, there was FRET interaction on Cy5-dsDNA-Cy3-$NH_2$ chip. The scanned images are shown in FIGS. 2g, 2h and 2i. Each spot on this chip theoretically had approximately equal numbers of Cy5 and Cy3 fluorophores. After cross-talk correction, the signals obtained from the FRET channel were strong. We used these fluorescence intensities from the Cy3 channel, Cy5 channel and FRET channel to determine the detection-correction factor G with the method described by equation 12. After the determination of the factors β and G, the proportional coefficient between G and $$\frac{1}{\beta}$$

can be calculated. Thus when we changed the scanning parameters, the new factor G can be determined simply by this coefficient and new values of β, and the factor β can be measured easily by the ratio of signal obtained from FRET channel to that obtained from Cy3 channel in the sample with only Cy3 present.

Fluorescence Measurement in Two-Color DNA Microarray Experiments

Figure 3:
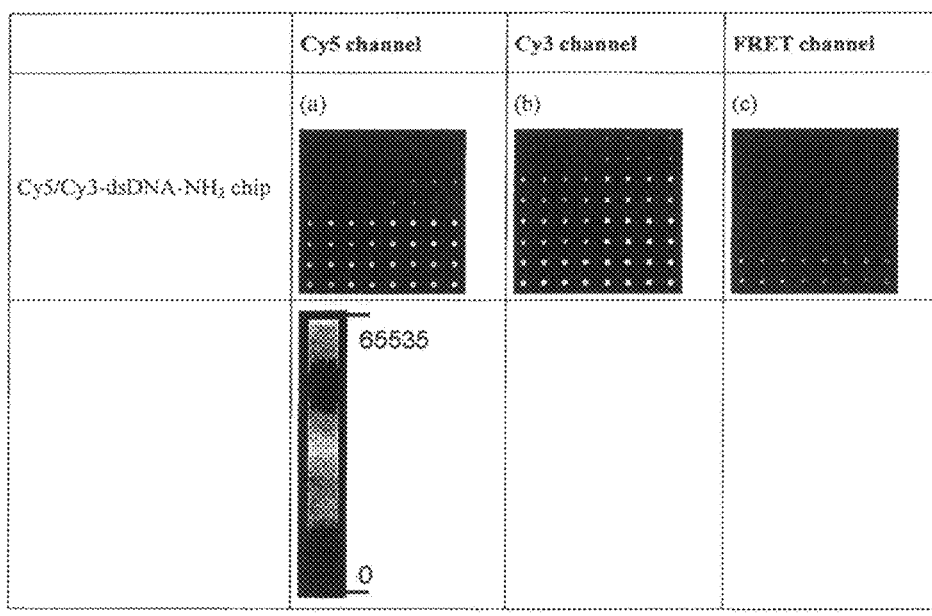
FIGS. 3(a)-(c) show the microarray images. The images were obtained by scanning Cy5/Cy3-dsDNA-$NH_2$ chip through Cy5 channel, Cy3 channel and FRET channel. Eight subarrays were used for the determination of the ratio of Cy5 to Cy3. The excitation power of 532 nm and 635 nm was set to 80. The PMT gains of 570 nm and 675 nm emission channels were both set to 650.
Figure 4:
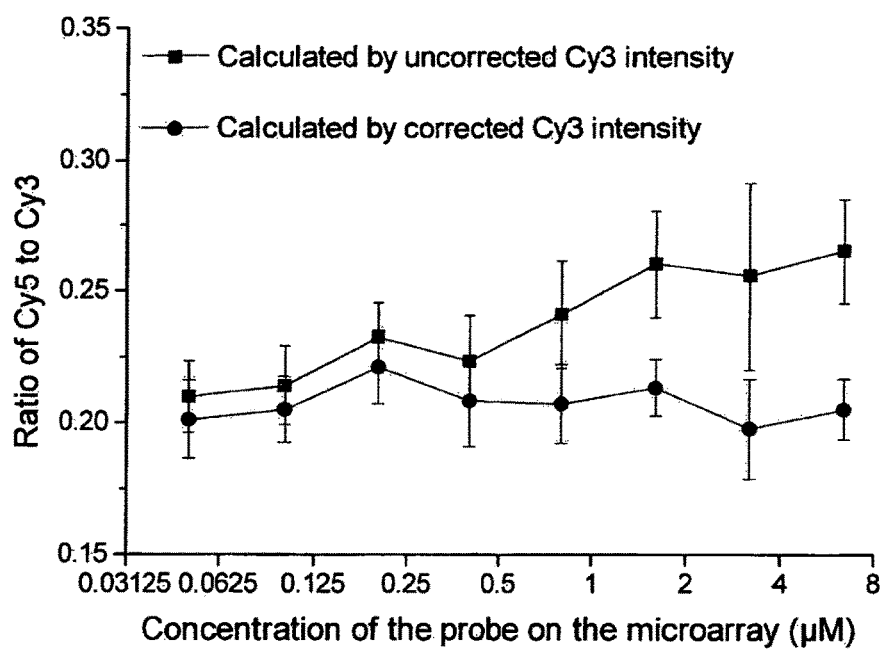
FIG. 4 shows the intensity ratio of Cy5 to Cy3 on Cy5/Cy3-dsDNA-$NH_2$ chip. Corrected Cy3 emission and uncorrected Cy3 emission of this chip were used for the calculation of the intensity ratio.

Having determined the system factors of the fluorescence scanner, reliable fluorescence measurement can be performed. In the two-color microarray experiments, it is usual that the Cy5- and Cy3-labeled DNA samples were hybridized with the probes in the same spot of the fabricated microarray chip. Due to the intermolecular FRET between Cy3 fluorophore and Cy5 fluorophore coupled respectively to closely adjacent double helixes, the fluorescence intensity of Cy3 will be potentially distorted. In the examples, we hybridized the mixture of Cy5-(oligo-1) and Cy3-(oligo-1) in the same concentration with (oligo-2)-$NH_2$ chip to fabricate Cy5/Cy3-dsDNA-$NH_2$ chip. The scanned fluorescence images are shown in FIGS. 3a, 3b and 3c. Because in the mixture (oligo-1)-Cy5 and (oligo-1)-Cy3 were in the same concentration and were hybridized with the same (oligo-2)-$NH_2$ chip, the density of Cy5 was approximately the same as that of Cy3 in each spot area due to the identical sequences and the same reaction conditions. The intensity ratio of Cy5 to Cy3 should remain constant when the concentration of the probes on the microarray chip changed. However, from FIG. 4 the ratio of Cy5 to Cy3 showed an increase as the concentration of probe increased. Because the probability of intermolecular FRET increased when the number of Cy3 and Cy5 increased on the same spot area of the microarray chip. After the calculation of the fluorescence intensity using equations 13 and 14, the ratio of Cy5 to Cy3 approximately remained constant when the concentration of the probe on the microarray chip increased. The results showed that fluorescence measurement is reliable in the two-color microarray experiments and can eliminate effectively the influence of FRET.

EXAMPLES

The present invention will be illustrated in further detail with reference to the example below. It is understood that this examples is illustrative only, and does not limit the scope of the invention.

Expression Profiling Arrays

The DNA microarray is a popular and effective method for simultaneous assaying the expression of large numbers of genes and is perfectly suited for the comparison of gene expression in different populations of cells. This biotechnology makes it possible to analyze quantitatively fluorescence signals representing the relative abundance of mRNA of two distinct samples. In a two-color procedure, two samples (e.g., treatment and control) are labeled with different fluorophores (usually Cy5 and Cy3 dyes) and hybridized together on a single microarray.

In a two-color procedure of a microarray-based expression profiling experiment, a custom DNA microarray is manufactured by spotting of cDNA fragments, arraying of prefabricated oligonucleotides or in situ synthesis of oligonucleotides. After each of mRNA from the treatment sample and the control sample is extracted, purified and reverse-transcribed to cDNA sample. Each cDNA sample is labeled with donor-dUTP (e.g., Cy3-dUTP for the control) or acceptor-dUTP (e.g., Cy5-dUTP for the treatment). Both donor- and acceptor-labeled cDNA samples are mixed and denatured. After free fluorescent nucleotides are removed, these labeled probes are hybridized to a pre-constructed cDNA microarray. After hybridization, the slides are washed and fluorescent images are acquired with two channels of a fluorescence scanner. If two samples have been labeled under similar conditions and labeling efficiencies of specific transcripts are similar in the two samples, it is possible to compare the relative abundance of the transcripts in the two samples. After analysis of scanned images, the ratio (e.g., Cy5/Cy3) is calculated for each spot and is normalized. Clustering analysis is performed to find out differential expression.

In this application, the dual-labeled mixture of treatment cDNA sample and control cDNA sample is hybridized with the oligonucleotides or cDNA fragments on the pre-constructed microarray chip. When the labeled targets from treatment sample and labeled targets from control sample are both bound with the probes in the same spot area on the chip, where the density of bound fluorophore-labeled cDNA samples is high enough, there will be distortions of donor (e.g., Cy3) signals due to intermolecular FRET. Hence, after the determination of the system factors of the microarray scanning system (e.g., Cy5 and Cy3 for the label of molecules and fluorescence scanner for the detection of fluorescence), arrays should be scanned with three channels, including conventional donor channel (e.g., Cy3 channel), conventional acceptor channel (e.g., Cy5 channel) and reconstructive FRET channel (e.g., excitation: Cy3 excitation wavelength, emission: Cy5 emission wavelength). Using our fluorescence measurement method, fluorescence intensity from Cy3 channel is corrected. Then we can calculate and normalize the ratio, and perform the clustering analysis.

The above example is illustrative of the invention described herein, and do not limit its scope.

REFERENCES CITED

U.S. Patent Documents
U.S. Pat. No. 6,661,909 B2 December 2003 Youvan, et al.
U.S. Pat. No. 7,209,836 April 2007 Schermer, et al.
Shalon, et al., *Genome Methods* (1996) 6: 639-645.
Gordon, et al., *Biophysical Journal* (1998) 74: 2702-2713.
Tu, et al., *Nucleic Acids Research* (1998) 26: 2797-2802.
Duggan, et al., *Nature Genetics Supplement* (1999) 21: 10-14.
Hegde, et al., *Biotechniques* (2000) 29: 548-562.
Yang, et al., *Nature Review Genetics* (2002) 3: 579-588.
Buschmann, et al., *Bioconjugate Chemisty* (2003) 14: 195-204.
Zal, et al., *Biophysical Journal* (2004) 86: 3923-3939.
Thaler, et al., *Biophysical Journal* (2005) 89: 2736-2749.
Lee, et al., *Biophysical Journal* (2005) 88: 2939-2953.
Chen, et al., *Biophysical Journal* (2006) 91: 39-41.
Patterson, et al., *Nature Biotechnology* (2006) 24:1140-1150.

What is claimed is:

1. A microarray chip for use in a two-color fluorescence measurement system, comprising three kinds of standard spots separate from each other on the microarray chip that are useful for determining correction factors for fluorescence measurements with the system, wherein the three standard spots comprise:

standard spot 1 comprising the donor fluorophore and none of the acceptor fluorophore used in the two-color fluorescence measurement system, wherein the donor fluorophore is immobilized on the microarray chip, standard spot 2 comprising the acceptor fluorophore and none of the donor fluorophore used in the two-color fluorescence measurement system, wherein the acceptor fluorophore is immobilized on the microarray chip, wherein the acceptor fluorophore in standard spot 2 is present in the same molar amount as the donor fluorophore in standard spot 1, and standard spot 3 comprising both the donor and the acceptor fluorophores immobilized on the microarray chip, wherein the molar amount of the donor fluorophore in standard spot 3 equals the molar amount of the acceptor fluorophore in standard spot 3.

2. The microarray chip of claim 1, wherein the donor fluorophore is Cy3 and the acceptor fluorophore is Cy5.

3. A method to make the microarray chip of claim 1, comprising preparing standard spot 3 by immobilizing on the chip a conjugate comprising a complex formed by contacting the donor fluorophore linked to a first binding pair member, and the acceptor fluorophore linked to a second binding pair member complementary to the first binding pair member, wherein the conjugate comprises equimolar amounts of the donor fluorophore and acceptor fluorophore linked together by the interaction between the first binding pair member and the second binding pair member.

4. The microarray chip of claim 1, wherein:
standard spot 1 comprises a first nucleic acid immobilized on the microarray chip and labeled with the donor fluorophore,
standard spot 2 comprises a second nucleic acid immobilized on the microarray chip and labeled with the acceptor fluorophore, and
standard spot 3 comprises a third nucleic acid immobilized on the microarray chip and labeled with both the donor fluorophore and the acceptor fluorophore.

5. A microarray chip for use in a two-color fluorescence measurement system, comprising two kinds of standard spots separate from each other on the microarray chip that are useful for determining correction factors for fluorescence measurements with the system, wherein the two standard spots comprise:
standard spot 1 comprising the donor fluorophore and no acceptor fluorophore, wherein the donor fluorophore is immobilized on the microarray chip, and
standard spot 2 comprising the acceptor fluorophore and no donor fluorophore, wherein the acceptor fluorophore is immobilized on the microarray chip,
wherein the acceptor fluorophore in standard spot 2 is present in the same molar amount as the donor fluorophore in standard spot 1.

6. The microarray chip of claim 5, wherein the donor fluorophore is Cy3 and the acceptor fluorophore is Cy5.

7. The microarray chip of claim 5, wherein:
standard spot 1 comprises a first nucleic acid immobilized on the microarray chip and labeled with the donor fluorophore, and
standard spot 2 comprises a second nucleic acid immobilized on the microarray chip and labeled with the acceptor fluorophore.

8. A system comprising:
a microarray chip for use in a two-color fluorescence measurement system, comprising three kinds of standard spots separate from each other on the microarray chip that are useful for determining correction factors for fluorescence measurements with the system, wherein the three standard spots comprise:
standard spot 1 comprising the donor fluorophore and none of the acceptor fluorophore used in the two-color fluorescence measurement system, wherein the donor fluorophore is immobilized on the microarray chip;
standard spot 2 comprising the acceptor fluorophore and none of the donor fluorophore used in the two-color fluorescence measurement system, wherein the acceptor fluorophore is immobilized on the microarray chip,
wherein the acceptor fluorophore in standard spot 2 is present in the same molar amount as the donor fluorophore in standard spot 1; and
standard spot 3 comprising both the donor and the acceptor fluorophores immobilized on the microarray chip, wherein the molar amount of the donor fluorophore in standard spot 3 equals the molar amount of the acceptor fluorophore in standard spot 3, and
a microarray fluorescence scanner that resolves fluorescence as a function of spatial coordinates in two dimensions, comprising:
a first fluorescence observation channel that provides excitation at a wavelength adapted for a first fluorophore, and a detector configured to detect the emission wavelength characteristic of the first fluorophore;
a second fluorescence observation channel that provides excitation at a wavelength adapted for a second fluorophore, and a detector configured to detect the emission wavelength characteristic of the second fluorophore; and
a third fluorescence observation channel that provides excitation at a wavelength adapted for the first fluorophore, and a detector configured to detect the emission wavelength characteristic of the second fluorophore.

9. The system of claim 8, wherein the first fluorophore is the donor fluorophore of a FRET fluorophore pair and the second fluorophore is the acceptor fluorophore of a FRET fluorophore pair, and wherein the first fluorophore is Cy3 and the second fluorophore is Cy5.

10. The system of claim 8, wherein:
standard spot 1 comprises a first nucleic acid immobilized on the microarray chip and labeled with the donor fluorophore,
standard spot 2 comprises a second nucleic acid immobilized on the microarray chip and labeled with the acceptor fluorophore, and
standard spot 3 comprises a third nucleic acid immobilized on the microarray chip and labeled with both the donor fluorophore and the acceptor fluorophore.

* * * * *

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 1
tccgtcatcg ctcaag                                                   16

<210> SEQ ID NO 2
<211> LENGTH: 16
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 3' -Cy5 fluorophore

<400> SEQUENCE: 2
tccgtcatcg ctcaag                                                        16

<210> SEQ ID NO 3
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: 3' -Cy3 fluorophore

<400> SEQUENCE: 3
tccgtcatcg ctcaag                                                        16

<210> SEQ ID NO 4
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: 5' -Cy5 fluorophore
<220> FEATURE:
<221> NAME/KEY: misc_feature
<223> OTHER INFORMATION: 3' -Cy3 fluorophore

<400> SEQUENCE: 4
tccgtcatcg ctcaag                                                        16

<210> SEQ ID NO 5
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 5
cttgagcgat gacggatttt tttttttttt tt                                      32

<210> SEQ ID NO 6
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: 3' -amine group

<400> SEQUENCE: 6
cttgagcgat gacggatttt tttttttttt tt                                      32
```